US006402781B1

(12) United States Patent
Langberg et al.

(10) Patent No.: US 6,402,781 B1
(45) Date of Patent: Jun. 11, 2002

(54) PERCUTANEOUS MITRAL ANNULOPLASTY AND CARDIAC REINFORCEMENT

(75) Inventors: Jonathan J. Langberg, Atlanta, GA (US); Michael D. Lesh, Mill Valley, CA (US)

(73) Assignee: Mitralife, Santa Rosa, CA (US)

( * ) Notice: Subject to any disclaimer, the term of this patent is extended or adjusted under 35 U.S.C. 154(b) by 0 days.

(21) Appl. No.: 09/494,233

(22) Filed: Jan. 31, 2000

(51) Int. Cl.[7] .................................................. A61F 2/06
(52) U.S. Cl. ...................... 623/2.36; 623/2.37; 623/1.11
(58) Field of Search ........................ 623/1.1, 1.11–1.54, 623/2.1–2.42

(56) References Cited

U.S. PATENT DOCUMENTS

| 4,128,100 A | 12/1978 | Wendorff |
| 4,917,698 A | 4/1990 | Carpentier et al. |
| 5,006,106 A | 4/1991 | Angelchik |
| 5,041,130 A | 8/1991 | Cosgrove et al. |
| 5,061,277 A | 10/1991 | Carpentier et al. |
| 5,064,431 A | 11/1991 | Gilbertson et al. |
| 5,099,838 A | 3/1992 | Bardy |
| 5,104,407 A | 4/1992 | Lam et al. |
| 5,163,955 A | 11/1992 | Love et al. |
| 5,165,403 A | 11/1992 | Mehra |
| 5,201,880 A | 4/1993 | Wright et al. |
| 5,290,300 A | 3/1994 | Cosgrove et al. |
| 5,350,420 A | 9/1994 | Cosgrove et al. |
| 5,450,860 A | 9/1995 | O'Connor |
| 5,476,471 A | 12/1995 | Shifrin et al. |

(List continued on next page.)

FOREIGN PATENT DOCUMENTS

| DE | 196 05 042 A1 | 1/1998 |
| EP | 0 727 239 A2 | 8/1996 |
| EP | 0 727 239 A3 | 6/1997 |
| WO | WO 91/19465 | 12/1991 |
| WO | WO 96/34211 | 10/1996 |

(List continued on next page.)

OTHER PUBLICATIONS

Boyd et al., "Tricuspid annuloplasty", Sep. 1974, The Journal of Thoracic and Cardiovascular Surgery, pp. 344–351.

Kurlansky et al., "Adjustable Annuloplasty for Tricuspid Insufficiency", Oct. 1987, The Annals of Thoracic Surgery, pp. 404–406.

Alonso–Lej, "Adjustable Annuloplasty for Tricuspid Insufficiency", Sep. 1988, The Annals of Thoracic Surgery, Letter to the Editor, pp. 368–369.

Chachques et al., "Latissimus Dorsi Dynamic Cardiomyoplasty, 1989, The Society of Thoracic Surgeons", pp. 600–604.

McCarthy et al., "Clinical experience with the Novacor ventricular assist system", May 1990, J Thorac Cardiovasc Surg, pp. 578–587.

Farrar et al., "A New Skeletal Muscle Linear–pull Energy Convertor as a Power Source for Prosthetic Circulatory Support Devices", Sep. 1992, The Journal of Heart and Lung Transplantation, pp. S341–S349.

(List continued on next page.)

*Primary Examiner*—David J. Isabella
*Assistant Examiner*—Urmi Chattopadhyay
(74) *Attorney, Agent, or Firm*—Knobbe, Martens, Olson & Bear, LLP

(57) ABSTRACT

A mitral annuloplasty and LV restriction device is designed to be transvenously advanced and deployed within the coronary sinus and in some embodiments other coronary veins. The device places tension on adjacent structures, reducing the diameter and/or limiting expansion of the mitral annulus and/or limiting diastolic expansion of the left ventricle. These effects may be beneficial for patients with dilated cardiomyopathy.

46 Claims, 10 Drawing Sheets

U.S. PATENT DOCUMENTS

| | | |
|---|---|---|
| 5,562,619 A | 10/1996 | Mirarchi et al. |
| 5,593,424 A | 1/1997 | Northrup, III |
| 5,702,343 A | 12/1997 | Alferness |
| 5,716,397 A | 2/1998 | Myers |
| 5,824,066 A | 10/1998 | Gross |
| 5,919,233 A | 7/1999 | Knopf et al. |
| 5,961,440 A | 10/1999 | Schweich, Jr et al. |
| 6,143,024 A | 1/2000 | Campbell et al. |
| 6,045,497 A | 4/2000 | Schweich, Jr et al. |
| 6,050,936 A | 4/2000 | Schweich, Jr et al. |
| 6,059,715 A | 5/2000 | Schweich, Jr. et al. |
| 6,077,214 A | 6/2000 | Mortier et al. |
| 6,095,968 A | 8/2000 | Snyders |
| 6,110,100 A | 8/2000 | Talpade |
| 6,123,662 A | 9/2000 | Alferness et al. |
| 6,146,325 A | 11/2000 | Lewis et al. |
| 6,155,968 A | 12/2000 | Wilk |
| 6,155,972 A | 12/2000 | Nauertz et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,122 A | 12/2000 | Alferness |
| 6,174,279 B1 | 1/2001 | Girard |
| 6,183,411 B1 | 2/2001 | Mortier et al. |
| 6,183,512 B1 | 2/2001 | Howanec, Jr. et al. |
| 6,193,648 B1 | 2/2001 | Krueger |
| 6,210,432 B1 * | 4/2001 | Solem et al. .............. 623/1.15 |
| 6,217,610 B1 | 4/2001 | Carpentier et al. |
| 6,221,103 B1 | 4/2001 | Melvin |
| 6,230,714 B1 | 5/2001 | Alferness et al. |
| 6,241,654 B1 | 6/2001 | Alferness |
| 6,250,308 B1 | 6/2001 | Cox |
| 6,260,552 B1 | 7/2001 | Mortier et al. |
| 6,261,222 B1 | 7/2001 | Mortier et al. |
| 6,264,602 B1 | 7/2001 | Mortier et al. |

FOREIGN PATENT DOCUMENTS

| | | |
|---|---|---|
| WO | WO 98/29041 | 7/1998 |
| WO | WO 99/30647 | 6/1999 |
| WO | WO 99/44534 | 9/1999 |
| WO | WO 00/06026 | 2/2000 |
| WO | WO 00/06027 | 2/2000 |
| WO | WO 00/06028 | 2/2000 |
| WO | WO 00/16700 | 3/2000 |
| WO | WO 00/18320 | 4/2000 |
| WO | WO 01/00111 A1 | 1/2001 |
| WO | WO 01/00114 A1 | 1/2001 |
| WO | WO 01/28455 A1 | 4/2001 |

OTHER PUBLICATIONS

Bolling et al., "Early outcome of mitral valve reconstruction in patients with end–stage cardiomyopathy", Apr. 1995, The Journal of Thoracic and Cardiovascular Surgery, pp. 676–683.

Bach et al., "Early improvement in congestive heart failure after correction of secondary mitral regurgitation in end–stage cardiomyopathy", Jun. 1995, American Heart Journal, pp. 1165–1170.

Bearnson et al., "Development of a Prototype Magnetically Suspended Rotor Ventricular Assist Device", ASAIO Journal 1996, pp. 275–280.

Batista et al., "Partial Left Ventriculetcomy to Improve Left Ventricular Function End–Stage Heart Disease", 1996, J Card Surg,, pp. 96–98.

Thoratec Ventricular Assist Device System, 1996, Brochure.

McCarthy et al., "Early Results with Partial Left Ventriculectomy", May 1997, Presented at the 77$^{th}$ Annual Meeting of the American Association of Thoracic Surgeons.

Buchanan et al., "Circumferential Suture of the Mitral Annulus for Correction of Mitral Regurgitation in Dogs", 1998, Veterinary Surgery vol. 27, pp. 182–193.

Yamani et al., "Surgical Treatment of Chronic Heart Failure", 2000, *Congestive Heart Failure Second Edition*, pp. 767–784.

Bristow et al., "Heart Failure Management Using Implantable Devices for Ventricular Resynchronization: Comparison of Medical Therapy, Pacing, and Defibrillation in Chronic Heart Failure (Companion) Trial," Sep. 2000, Journal of Cardiac Failure vol. 6, No. 3, pp. 276–285.

Smolens et al., "Mitral Valve Repair in Heart Failure," 2000, European Journal of Heart Failure 2, pp. 365–371.

* cited by examiner

PERCUTANEOUS MITRAL ANNULOPLASTY AND CARDIAC REINFORCEMENT

The present invention relates to intravascular prostheses for remodeling an extravascular anatomical structure. In one application, the present invention relates to a mitral annuloplasty and cardiac reinforcement device which is transluminally implantable in the coronary sinus.

BACKGROUND OF THE INVENTION

Dilated cardiomyopathy occurs as a consequence of many different disease processes that impair myocardial function, such as coronary artery disease and hypertension. The left ventricle enlarges and the ejection fraction is reduced. The resulting increase in pulmonary venous pressure and reduction in cardiac output cause congestive heart failure. Enlargement of the mitral annulus and left ventricular cavity produce mitral valvular insufficiency, This in turn, causes volume overload that exacerbates the myopathy, leading to a vicious cycle of progressive enlargement and worsening mitral regurgitation.

According to recent estimates, more than 79,000 patients are diagnosed with aortic and mitral valve disease in U.S. hospitals each year. More than 49,000 mitral valve or aortic valve replacement procedures are performed annually in the U.S., along with a significant number of heart valve repair procedures.

Various surgical techniques have been developed to repair a diseased or damaged valve. One repair technique which has been shown to be effective in treating incompetence, particularly of the mitral and tricuspid valves, is annuloplasty, in which the effective size of the valve annulus is contracted by attaching a prosthetic annuloplasty ring to the endocardial surface of the heart around the valve annulus. The annuloplasty ring comprises an inner substrate of a metal such as stainless steel or titanium, or a flexible material such as silicone rubber or Dacron cordage, covered with a biocompatible fabric or cloth to allow the ring to be sutured to the heart tissue. The annuloplasty ring may be stiff or flexible, may be split or continuous, and may have a variety of shapes, including circular, D-shaped, C-shaped, or kidney-shaped. Examples are seen in U.S. Pat. Nos. 4,917,698, 5,061,277, 5,290,300, 5,350,420, 5,104,407, 5,064,431, 5,201,880, and 5,041,130, which are incorporated herein by reference.

Annuloplasty rings may also be utilized in combination with other repair techniques such as resection, in which a portion of a valve leaflet is excised, the remaining portions of the leaflet are sewn back together, and a prosthetic annuloplasty ring is then attached to the valve annulus to maintain the contracted size of the valve. Other valve repair techniques in current use include commissurotomy (cutting the valve commissures to separate fused valve leaflets), shortening mitral or tricuspid valve chordae tendonae, reattachment of severed mitral or tricuspid valve chordae tendonae or papillary muscle tissue, and decalcification of the valve leaflets or annulus. Annuloplasty rings may be used in conjunction with any repair procedures where contracting or stabilizing the valve annulus might be desirable.

Although mitral valve repair and replacement can successfully treat many patients with mitral valvular insufficiency, techniques currently in use are attended by significant morbidity and mortality. Most valve repair and replacement procedures require a thoracotomy, usually in the form of a median sternotomy, to gain access into the patient's thoracic cavity. A saw or other cutting instrument is used to cut the sternum longitudinally, allowing the two opposing halves of the anterior or ventral portion of the rib cage to be spread apart. A large opening into the thoracic cavity is thus created, through which the surgical team may directly visualize and operate upon the heart and other thoracic contents. Alternatively, a thoracotomy may be performed on a lateral side of the chest, wherein a large incision is made generally parallel to the ribs, and the ribs are spread apart and/or removed in the region of the incision to create a large enough opening to facilitate the surgery.

Surgical intervention within the heart generally requires isolation of the heart and coronary blood vessels from the remainder of the arterial system, and arrest of cardiac function. Usually, the heart is isolated from the arterial system by introducing an external aortic cross-clamp through a sternotomy and applying it to the aorta to occlude the aortic lumen between the brachiocephalic artery and the coronary ostia. Cardioplegic fluid is then injected into the coronary arteries, either directly into the coronary ostia or through a puncture in the ascending aorta, to arrest cardiac function. The patient is placed on extracorporeal cardiopulmonary bypass to maintain peripheral circulation of oxygenated blood.

Of particular interest in the present application are techniques for the repair and replacement of the mitral valve. The mitral valve, located between the left atrium and left ventricle of the heart, is most easily reached through the wall of the left atrium, which normally resides on the posterior side of the heart, opposite the side of the heart that is exposed by a median sternotomy. Therefore, to access the mitral valve via a sternotomy, the heart is rotated to bring the left atrium into an anterior position. An opening, or atriotomy, is then made in the right side of the left atrium, anterior to the right pulmonary veins. The atriotomy is retracted by means of sutures or a retraction device, exposing the mitral valve adjacent to the atriotomy. One of the previously identified techniques may then be used to repair or replace the valve.

An alternative technique for mitral valve access has been used when a median sternotomy and/or rotational manipulation of the heart are inappropriate. In this technique, a thoracotomy is made in the right lateral side of the chest, usually in the region of the fourth or fifth intercostal space. One or more ribs may be removed from the patient, and other ribs near the incision are retracted outward to create a large opening into the thoracic cavity. The left atrium is then exposed on the posterior side of the heart, and an atriotomy is formed in the wall of the left atrium, through which the mitral valve may be accessed for repair or replacement.

Using such open-chest techniques, the large opening provided by a median sternotomy or right thoracotomy enables the surgeon to see the mitral valve directly through the left atriotomy, and to position his or her hands within the thoracic cavity in close proximity to the exterior of the heart for cannulation of the aorta and/or coronary arteries to induce cardioplegia, manipulation of surgical instruments, removal of excised tissue, and introduction of an annuloplasty ring or a replacement valve through the atriotomy for attachment within the heart.

Mitral valve surgery, including mitral annuloplasty, is usually applied to patients with intrinsic disease of the mitral apparatus. As described above, these patients may have scarring, retraction, tears or fusion of valve leaflets as well as disorders of the subvalvular apparatus. Definitive repair requires direct visualization of the valve.

Patients who develop mitral regurgitation as a result of dilated cardiomyopathy do not have intrinsic mitral valve disease. Regurgitation occurs as the result of the leaflets being moved back from each other by the dilated annulus. The ventricle enlarges and becomes spherical, pulling the papillary muscles and chordae away from the plane of the valve and further enlarging the regurgitant orifice. In these patients, correction of the regurgitation does not require repair of the valve leaflets themselves, but simply a reduction in the size of the annulus and the sphericity of the left ventricle.

Mitral annuloplasty without repair of the leaflets or chordae has been shown to be effective in patients with dilated cardiomyopathy who are refractory to conventional medical therapy. Bolling and coworkers have operated on a cohort of such patients with New York Heart Association Class III and IV symptoms. Average symptom severity decreased from 3.9 preoperatively to 2.0 after surgery. Hemodynamics and ejection fraction improved significantly. Other investigators have achieved similar results as well. However, the morbidity, risks and expense of surgical annuloplasty are very high in patients with cardiomyopathy and congestive heart failure. Thus, a variety of new techniques for the treatment of congestive heart failure are being explored as adjuncts to drug therapy.

Several cardiac restraint devices have been described. U.S. Pat. No. 5,702,343 to Alferness discloses a cardiac reinforcement device that is applied as a jacket over the epicardium in order to limit diastolic expansion. However, this requires an open chest operation to implant and does not directly affect the diameter of the mitral annulus. Another approach is disclosed in U.S. Pat. No. 5,961,440 to Schweich, et al., in which tension members are placed through opposite walls of the heart such that they span the ventricle. Less invasive and "minimally" invasive techniques for valve repair and replacement continue to evolve, both on a stopped heart and on a beating hearts These techniques may provide some benefits over open chest procedures, but they are still attended by significant morbidity and mortality risks.

A need therefore remains for methods and devices for treating mitral valvular insufficiency, which are attended by significantly lower morbidity and mortality rates than are the current techniques, and therefore would be well suited to treat patients with dilated cardiomyopathy. Optimally, the procedure can be accomplished through a percutaneous, transluminal approach, using simple, implantable devices which do not depend upon prosthetic valve leaflets or other moving parts.

SUMMARY OF THE INVENTION

There is provided in accordance with one aspect of the present invention, a method of treating mitral valvular insufficiency. The method comprises the steps of transvenously advancing a prosthesis into the coronary sinus, and deploying at least a portion of the prosthesis within the coronary sinus to reduce the diameter of the mitral annulus. Although deployment can be accomplished in an open surgical procedure, the method preferably further comprises the step of percutaneously accessing the venous system prior to the transluminally advancing step. The venous system may be accessed by one of the internal jugular, subdlavian, or femoral veins. Preferably, the deploying step further includes the step of advancing the prosthesis from a first configuration for transluminal implantation to a second configuration to apply pressure to the wall of the coronary sinus and thereby reduce and/or restrain the diameter of the mitral valve annulus.

In accordance with another aspect of the present invention, there is provided a method of performing transluminal mitral annuloplasty. The method comprises the steps of providing a catheter which carries a prosthesis, and percutaneously inserting the catheter into the venous system. The prosthesis is transluminally advanced into the coronary sinus, and deployed in the coronary sinus to influence the size of the mitral valve annulus. Preferably, the prosthesis is caused to exert a compressive force on the mitral valve annulus.

The compressive force of one embodiment is generated by a bias in the prosthesis. In an alternate embodiment, the compressive force is generated by tightening the prosthesis around the mitral valve annulus following the transluminally advancing step. The tightening step may be accomplished by axial movement of a tightening element with respect to the prosthesis.

In accordance with a further aspect of the present invention, there is provided a method of providing a therapeutic compressive force against a tissue structure which is distinct from a vessel wall. The method comprises the steps of positioning a device in the vessel, and exerting a force against the wall of the vessel to exert a force against an extravascular tissue structure. Preferably, the positioning step is accomplished percutaneously. In one application, the extravascular tissue structure comprises the mitral valve annulus. Thus, the present invention provides a method of performing annuloplasty of the mitral valve, comprising positioning a prosthesis in the venous sinus.

In accordance with another aspect of the present invention, there is provided an implant for extravascular remodeling, for positioning within a vascular structure to influence tissue outside of the vessel. The implant comprises an elongate flexible support, having a proximal end and a distal end. Each of the proximal and distal ends are dimensioned to reside completely within the vascular system. A forming element is attached to the support, such that movement of the forming element relative to the support changes the shape of the support. The support is thus moveable between an implantation configuration for transluminal implantation and a remodeling configuration for exerting a force against a vessel wall. In one application, the support defines an arc when in the remodeling configuration.

Preferably, the implant for extravascular remodeling further comprises a lock for restraining the support in the remodeling configuration. In one embodiment, the lock comprises a locking ring. Alternatively, the lock comprises a compression fit, an interference fit or an adhesive bond.

The support is moveable from the implantation configuration to the remodeling configuration in response to movement of a remodeling control such as proximal retraction of the forming element. Alternatively, the support is moveable from the implantation configuration to the remodeling configuration in response to distal advancement of the forming element.

In one embodiment, the implant for extravascular remodeling further comprises an anchor for retaining the implant at a deployment site within a vessel. In one application, the anchor comprises a distal extension of the support, for positioning within the great cardiac vein. Alternatively, the anchor comprises a friction enhancing surface texture or structure for engaging the wall of the vessel. In a further embodiment, the anchor comprises at least one barb for piercing the wall of the vessel.

In accordance with yet a further aspect of the present invention, there is provided a transluminally implantable annuloplasty device. The annuloplasty device comprises a flexible body, having a proximal end and a distal end. An annuloplasty zone is provided on a proximal portion of the body, and an anchor zone is provided on a distal portion of the body. An axially moveable forming element is attached to the body between a mid-point of the annuloplasty zone and a mid-point of the anchor zone, such that proximal retraction of the forming element with respect to the proximal end of the body advances at least the annuloplasty zone into an arcuate configuration.

In accordance with a further aspect of the present invention, there is provided a method of treating a mitral valve. The method comprises the steps of providing an elongate flexible vascular implant, having a first attachment site spaced axially apart from a second attachment site. The first attachment site is transluminally advanced through the coronary sinus and coronary venous system to form the implant into an open loop. The open loop is reduced in size to place tension on the coronary sinus, and the first attachment site is attached to the second attachment site to close the loop and retain tension on the coronary sinus.

In accordance with another aspect of the present invention, there is provided a method of treating the heart. The method comprises the steps of advancing an implant through an access site and into a coronary vein such as the coronary sinus. A forming element on the implant is thereafter proximally retracted while resisting proximal movement of the implant, thereby forming the implant into a desired shape. The access site is thereafter closed, leaving the formed implant within the coronary vein.

Preferably, the method further comprises the step of locking the implant into the desired shape prior to the closing step. The method may additionally comprise the step of severing at least a portion of the forming element prior to the closing step.

Further features and advantages of the present invention will become apparent to those of ordinary skill in the art in view of the detailed description of preferred embodiments which follows, when considered together with the attached drawings and claims.

DETAILED DESCRIPTION OF PREFERRED EMBODIMENTS

The present invention provides a method and apparatus for performing mitral annuloplasty and remodeling of the left ventricle using a device that may be introduced percutaneously, and placed within the coronary venous system of the heart. The device exerts compressive force on the mitral annulus and left ventricle, reducing the severity of mitral regurgitation and the size of the left ventricular cavity. The device thus enables reduction of the mitral annulus and constraint of the diastolic expansion of the left ventricle yet without the morbidity and other risks associated with open chest surgery.

The present inventors have determined that the coronary sinus and veins provide an ideal conduit for the positioning of an intravascular prosthesis for remodeling the mitral annulus, since they are positioned adjacent the mitral annulus and interventricular septum. The cpronary sinus is contained within the atrioventricular groove, and is in close proximity to the posterior, lateral and anterior aspects of the mitral annulus. The coronary sinus and coronary veins are cannulated currently during any of a variety of percutaneous transvenous diagnostic and therapeutic procedures. Permanent placement of pacemaker and defibrillator leads within the coronary sinus and veins is both safe and well tolerated.

The annuloplasty system consists of several components. There is a delivery system intended to be introduced percutaneously into a central vein such as the internal jugular, subdlavian or femoral veins and to cannulate the coronary sinus. The implant of the present invention is deployed from the delivery catheter into the coronary venous system. Additional tools may be placed through or along the delivery catheter to position the device, apply elements in place, and to control and/or cut the tensioning elements from the delivery system as will be discussed.

Figure 1:
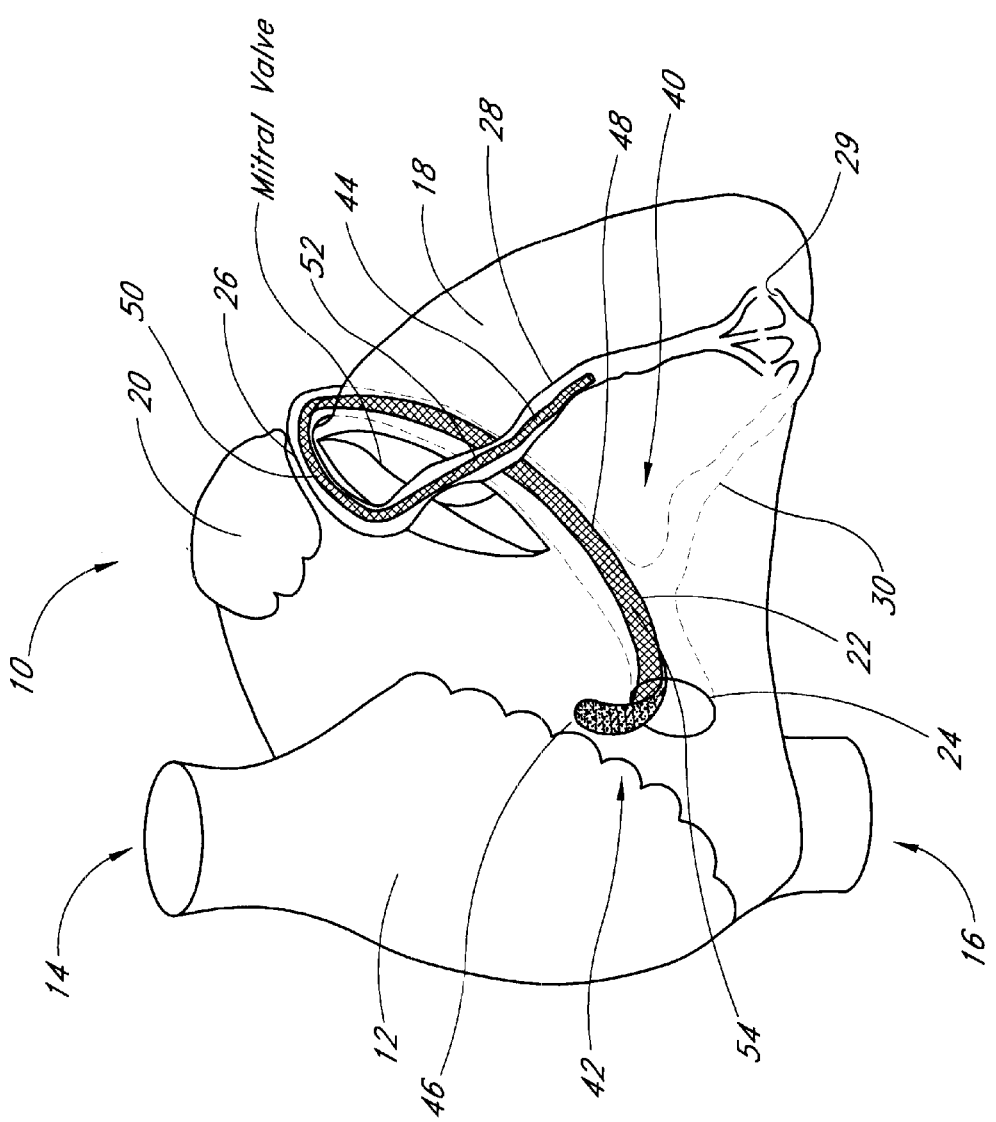
FIG. 1 is a schematic illustration of the heart, showing one embodiment of the mitral annuloplasty device of the present invention deployed within the coronary venous system.

Referring to FIG. 1, there is illustrated a schematic view of the heart 10, having a mitral annuloplasty and cardiac reinforcement device 40 positioned therein. The heart 10 generally comprises a right atrium 12, in communication with the superior vena cava 14 and inferior vena cava 16. The left ventricle 18 is positioned below the left atrial appendage 20. Relevant portions of the coronary vasculature include the coronary sinus 22, which extends from the ostium 24 to the junction 26 of the coronary sinus and the great cardiac vein 28. There may be anastomotic connections 29 between the great cardiac vein 28 and the middle cardiac vein 30, as is well understood in the art.

One embodiment of a mitral annuloplasty and cardiac reinforcement device 40 in accordance with the present invention is illustrated generally in the coronary sinus 22. In particular, the device 40 extends from a proximal end 42 to a distal end 44. The proximal end 42 lies against the posterior aspect of the interatrial septum 46. The midportion 48 of the device 40 is positioned within the coronary sinus 22. The transitional section 50 of the device 40 lies at the junction 26 of the coronary sinus 22 and the great cardiac vein 28. The distal end 44 of the device 40 is lodged in the great cardiac vein 28.

The transitional region 50 is designed to reside in the proximal portion of the great cardiac vein 28. By deflecting out of the plane of the coronary sinus 22, it serves as an anchor 52 and prevents the device 40 from slipping out of the coronary sinus 22 when tension is applied. This embodiment of an anchor 52 is very flaccid and flexible, thereby minimizing the risk of erosion of the device 40 through the wall of the great cardiac vein or other aspect of the coronary venous system. The proximal end 42 of the device 40 lies outside the ostium 24 of the coronary sinus 22 and is curved upward so as to anchor against the posterior aspect of the interatrial septum 46. The proximal end 42 is semicircular in shape and elliptical in profile so that no edges will promote erosion of adjacent tissue.

As an alternative anchor 52 to the distal extension of the device 40, any of a variety of structures may be provided. In general, the deployed device 40 will contact the wall of the coronary sinus 22 along the inside radius of its arcuate path. Thus, a tissue contacting surface 54 on the concave side of the deployed device 40 may be provided with any of a variety of friction enhancing surface structures, such as a plurality of transverse ridges, teeth or other projections, or modified surface textures to enhance friction. Alternatively, tissue engaging or piercing structures such as barbs may be provided on the surface 54 to engage the wall of the coronary sinus 22 to resist movement of the device 40.

The specific dimensions, construction details and materials for the mitral annuloplasty and cardiac reinforcement device 40 can be varied widely, as will be appreciated by those of skill in the art in view of the disclosure herein. For example, dimensional adjustments may be made to accommodate different anatomical sizes and configurations. Materials and construction details can be varied to accommodate different tensioning mechanisms and other considerations.

Figure 2:
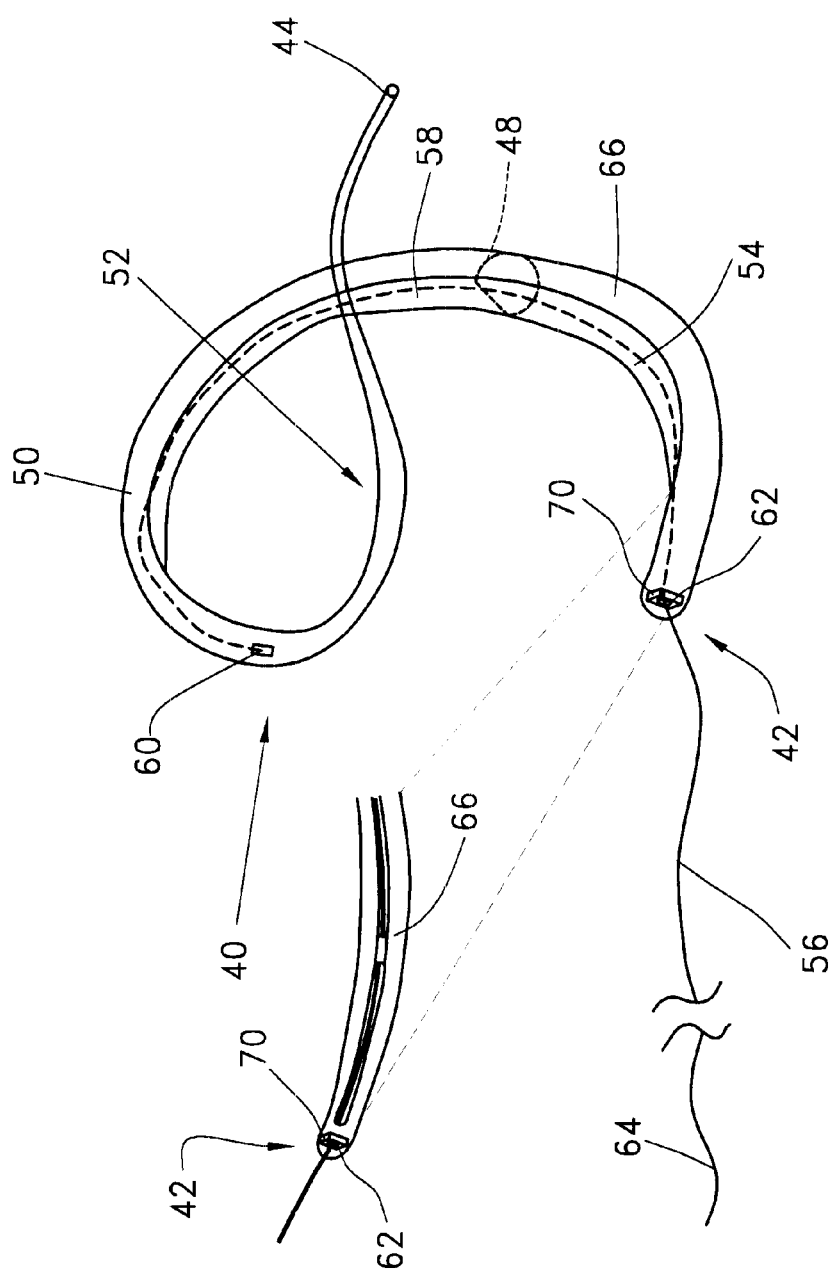
FIG. 2 is a schematic illustration of the mitral annuloplasty device shown in FIG. 1.
Figure 2A:
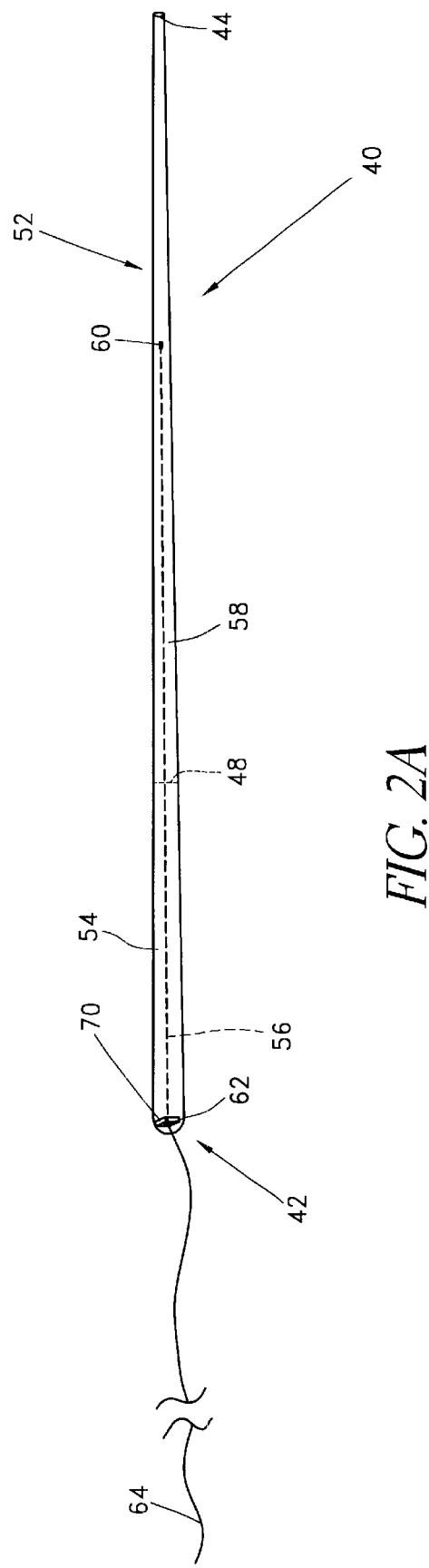
FIG. 2A is a schematic illustration of the mitral annuloplasty device shown in FIG. 2, in a linear configuration.

In general, the device 40 has an overall length from proximal end 42 to distal end 44 within the range of from about 2 cm to about 10 cm, in an embodiment such as that illustrated in FIG. 2 in which the anchor 52 comprises a distal extension of the body 66 for lodging within the great cardiac vein 28. One embodiment of the device 40 includes an elongate flexible body 66 about eight centimeters in length. In this embodiment, the body 66 is preferably elliptical in cross section so that it will bend in the plane of the coronary sinus 22 and mitral annulus when force is applied to the tensioning element within it (discussed below). Distally the device tapers and transitions to a round cross-section.

Referring to FIG. 2, there is illustrated an embodiment of the device 40 having a forming element 56 therein. Manipulation of the forming element 56 allows the device to be moved from a flexible orientation to enable percutaneous insertion into the vascular system and navigation into the coronary sinus, to an arcuate configuration for compressing at least a portion of the mitral annulus. The device 40 may be advanced from the first, flexible configuration to the second, arcuate configuration by either axial proximal retraction or distal advancement of the forming element 56 with respect to the body 66, depending upon the particular design.

In general, the device 40 comprises an elongate flexible support 58, extending from a proximal end 42 at least as far as a point of attachment 60. The support 58 may be a portion of the body 66 or may be a distinct component as will be discussed. The support 58 has a fixed length, and is relatively axially non compressible or expandable. Thus, proximal retraction of the forming element 56 compared to the proximal end of the support 58 will cause the support 58 to deflect in a first direction. Distal axial advancement of the forming element 56 with respect to the support 58 will cause lateral deflection of the support 58 in a second direction. This basic steering configuration can be embodied in many forms, which can be optimized by those of skill in the art to suit a particular construction for the body 66 depending upon the desired dimensions and clinical performance.

The forming element 56 extends from the proximal end 42 through the device 40 to the point of attachment 60. At the point of attachment 60, the forming element 56 is mechanically linked, and preferably, directly linked to the support 58. A proximal extension 64 of the forming element 56 extends from the proximal end 42 of the device 40, such as through an aperture 62. Proximal retraction of the forming element 56 through the aperture 62 causes the device 40 to bend from an implantation orientation for navigating the coronary vasculature during implantation to a formed orientation for compression and constraint of the coronary sinus 22 and adjacent structures.

In the formed orientation, the device 40 preferably provides a compressive force against the mitral annulus as has been discussed. This is accomplished by forming the device into an arcuate configuration. Generally, the best fit curve of constant radius to which the formed device conforms has a radius within the range of from about 1.0 cm to about 2.0 cm.

The forming element may comprise any of a variety of components, such as a polymeric or metal wire or strand, a multifilament braided or woven line, a metal or polymeric ribbon, or other structure capable of retaining the device 40 under tension in the coronary sinus 22.

The device 40 further comprises a support 58, which may be the body 66 of the device 40 or a separate element positioned therein. In an embodiment in which the support 58 is a separate element contained within the device 40, support 58 may comprise any of a variety of generally axially non-compressible elements such as a metal or polymeric wire or column, ribbon, or "bottomed out" spring which facilitates lateral bending but inhibits axial compression upon proximal retraction of forming element 56. A metal ribbon comprising stainless steel, nitinol, or other known materials may be desired in certain embodiments, due to its ability to influence the plane of curvature of the device 40 when in the formed orientation.

Figure 7:
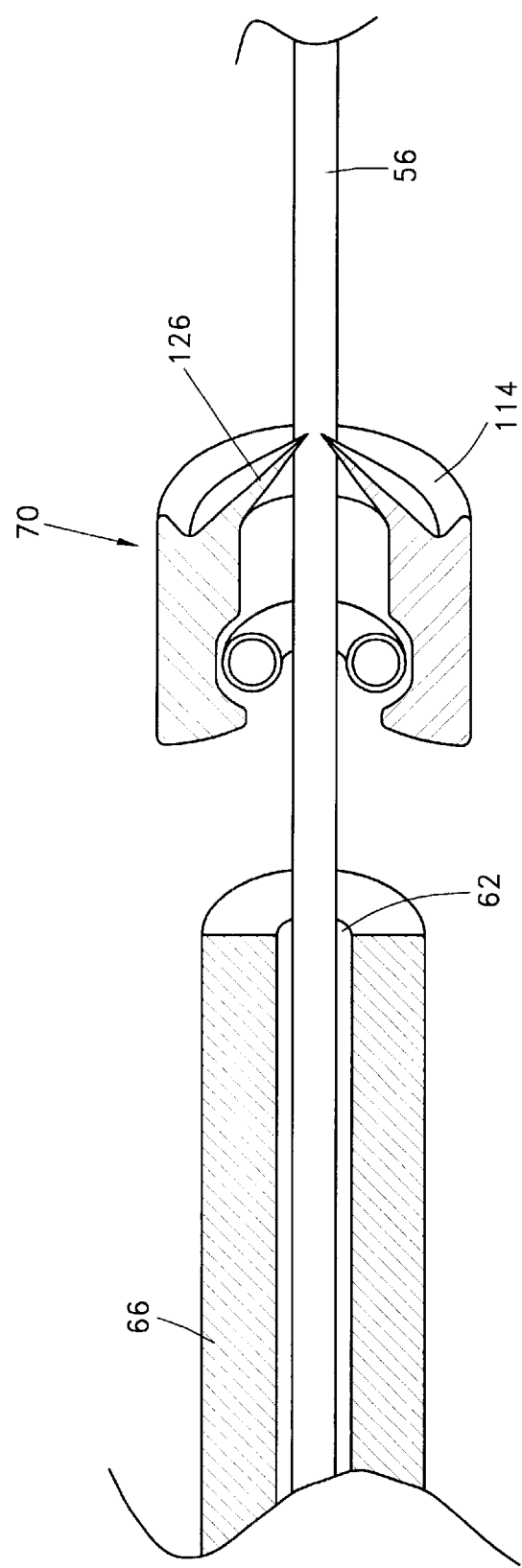
FIG. 7 is a schematic cross-sectional view of one embodiment of a locking device in accordance with the present invention.

The proximal extension 64 of the forming element 56 extends proximally throughout the length of the deployment catheter, to a control or free end which remains outside of the patient during the deployment procedure. Following placement of the device 40 in the coronary sinus, proximal traction on the proximal extension 64 will reconfigure the device 40 into the formed orientation within the coronary sinus, as will be discussed in connection with the method of the present invention. After a sufficient tension has been placed on the coronary sinus, the forming element 56 is preferably axially locked to the device 40, to resist distal movement of the forming element 56 through aperture 62. Any of a variety of locks 70 may be provided. Preferably, the lock 70 is provided on or near the proximal end 42, and, in particular, at or about the aperture 62 (FIG. 7). The lock may comprise any of a variety of structures, such as a suture knot, locking clamp or ring, an interference fit, ratchet and pall structures, an adhesive bond, or a compression fit, as will be apparent to those of skill in the art in view of the disclosure herein.

The lock 70 (on any of the embodiments herein) may be initially disengaged, so that the forming element 56 may be retracted or advanced freely through the aperture 62 while the physician adjusts the tension on the device 40. After the desired tension is achieved, the lock 70 is activated to engage the forming element in a manner which will depend upon the lock design. Alternatively, the lock 70 may be biased into an engaged configuration, such as with ratchet or cam structures, so that the forming element can only be retracted proximally. Preferably, however, the lock will allow the forming element to be released so that the physician can release tension in the device 40 in the event of momentary over tightening.

Figure 8:
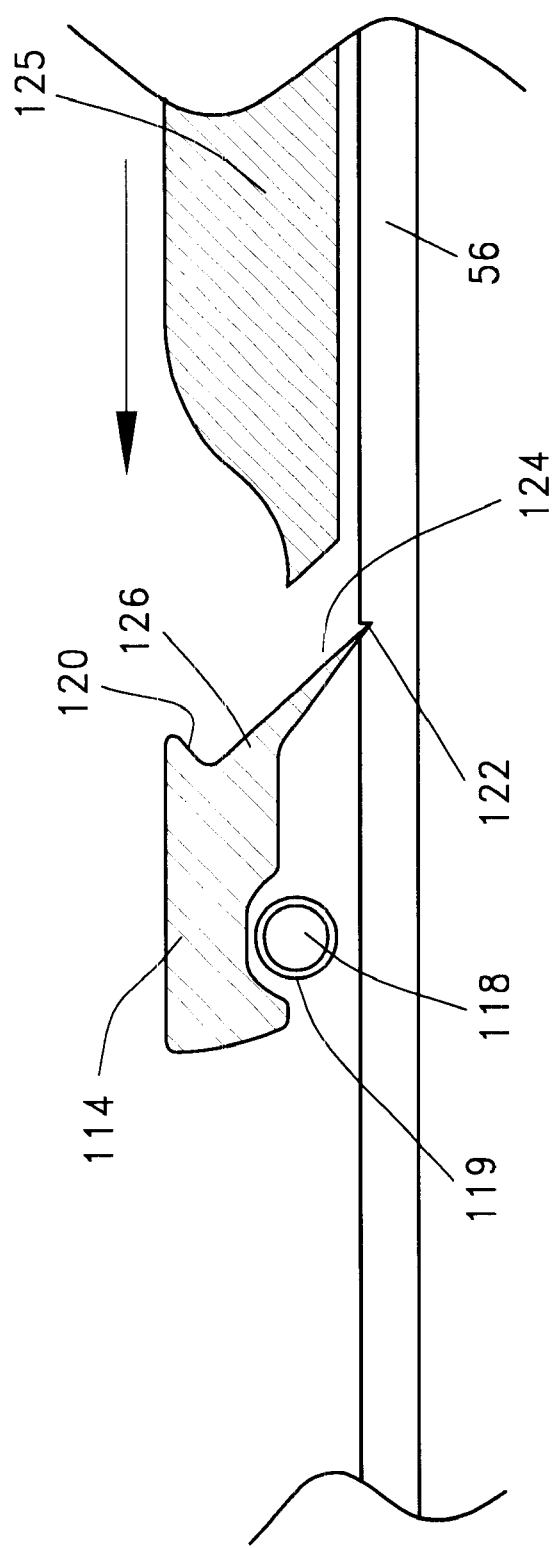
FIG. 8 is a fragmentary view of a portion of the lock illustrated in FIG. 7, with a locking tool.
Figure 9:
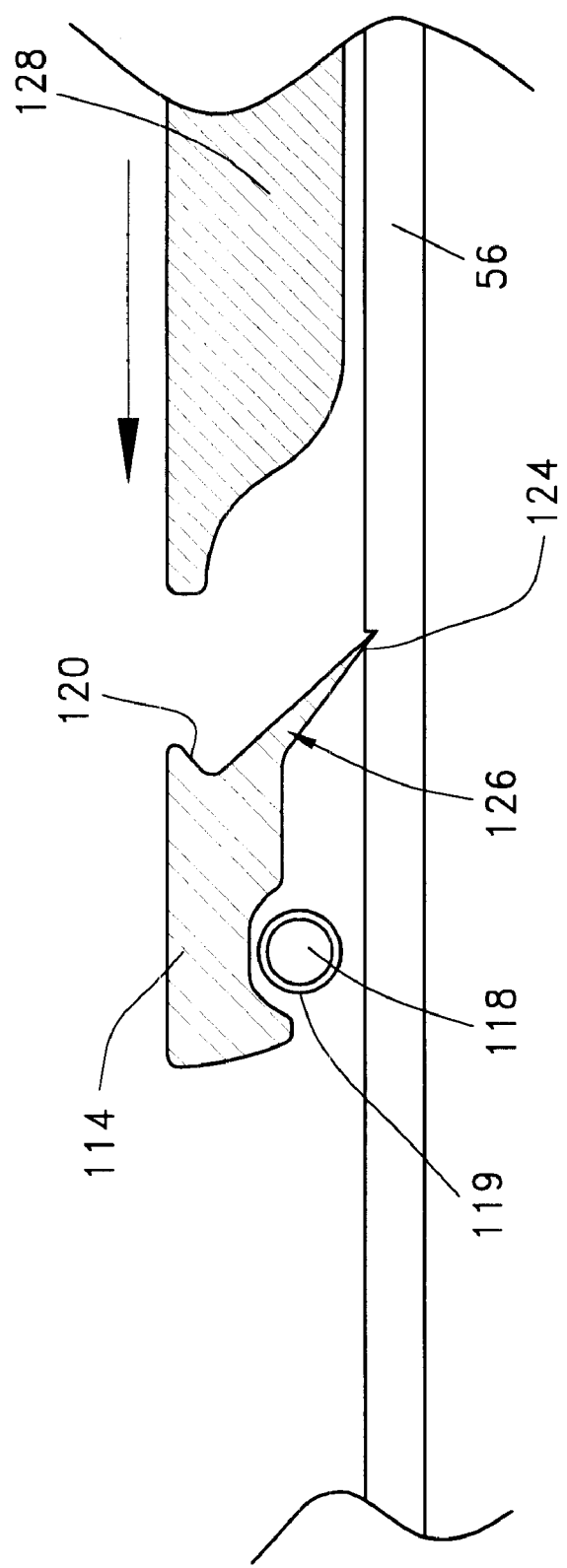
FIG. 9 is a fragmentary view as in FIG. 8, showing an unlocking tool.

Referring to FIGS. 7–9, there is disclosed one embodiment of a releasable lock 70 in accordance with the present invention. Although the lock 70 is illustrated as a discrete component of the system, it can alternatively be formed integrally with or attached to the proximal end of the body 66. The lock 70 comprises a body 114, which may be in the form of an annular collar with a central aperture for axial movement over the forming element 56. The body 114 is provided with one or two or three or more releasable locking elements 126 which ramp radially inwardly in the proximal direction.

Each locking element 126 is provided with at least one engagement surface 122 for engaging the forming element 56. The forming element 56 may be provided with any of a variety of friction enhancing surface textures or structures to enhance the locking function. Thus, a locking zone along the forming element may be provided with an etched surface or friction enhancing coating. Alternatively, structures such as a plurality of beads or teeth can be provided to permit an interference fit with the engagement surface 122.

The engagement surface 122 is movable between a first, disengaged configuration and a second, engaged configuration. This may be accomplished by pivoting the locking element 126 about a fulcrum 118. In the illustrated embodiment, fulcrum 118 is formed by an annular ring 119. Alternatively, the fulcrum 118 can be formed by plastic deformation of an integral structure, such as a living hinge formed by one or more annular grooves in the body 114.

The locking elements 126 may be biased in the locked direction, unlocked direction, or neutrally. Locking may be accomplished by pressing distally on a locking surface 124 such as with a locking tool 125 (FIG. 8) which applies distal pressure on the ramped locking element 126 at a point which is displaced radially inwardly from the fulcrum 118. Unlocking may be accomplished by distally advancing an unlocking tool 128 against a release surface 120 which is displaced radially outwardly from the fulcrum 118. In one embodiment, the locking tool 125 and unlocking tool 128 are conveniently formed from concentric tubular elements as will be apparent to those of skill in the art. The tubular elements or proximally extending control wires extend proximally to controls outside of the patient. Alternatively, any of a variety of ramped engagement surfaces and tools can be readily configured to accomplish the lock and/or release functions in view of the disclosure herein.

The length of the device 40 from proximal end 42 through the point of attachment 60 is generally within the range of from about 2 cm to about 10 cm, and, preferably within the range of from about 6 cm to about 8 cm. The shape of the device 40 is preferably designed to minimize trauma to the vascular intima, both during implantation and following placement. This may be accomplished by rounding all edges which may come into contact with the vessel wall. Thus, the cross-section through the mid portion 48 of the device, for example, may be elliptical, semicircular or otherwise rounded, or rectangular with rounded corners. In general, the maximum cross-section of the device 40 will be no more than about 15 mm$^2$, and preferably no more than about 10 mm$^2$, for implantation within a human adult.

The device 40 may be manufactured in accordance with any of a variety of techniques, which will be apparent to those of skill in the art in view of the disclosure herein. For example, the body 66 may be formed by extrusion, injection molding, or other techniques. In one embodiment, the forming element 56 is secured at point of attachment 60 to an elongate flexible support 58 and coextruded within a polymeric body 66. Alternatively, the forming element 56 and support 58 subassembly may be positioned within a mold cavity, and injection molded to produce the final device 40. The body 66 may comprise any of a variety of biocompatible materials such as various densities of polyethylenes, nylon, polyethylene terepbthalate, PEBAX, and others which will be apparent to those of skill in the art.

Alternatively, the forming element 56 and support 58 may be surrounded by a tubular jacket of ePTFE or Dacron fabric, or other material which is wrapped or stitched onto the forming element 56 to produce the final device 40. As a further alternative, the subassembly which includes the forming element 56 and, if present, support 58 may be positioned within a suitable length of tubing formed such as by extrusion. The tubing may be drawn down to a reduced diameter at the distal end 44. Additional post extrusion steps may be used to produce the desired cross-sectional configuration. Manufacturing techniques for the present invention will be apparent to those of skill in the art in view of the disclosure herein.

Any of a variety of additional features may be added to the device 40, depending upon the desired clinical performance. For example, the outside surface of the body 66 may be provided with any of a variety of coatings, such as Paralene, PTFE or others to improve lubricity; heparin or other antithrombogenic agents; elastomers such as silicone, neoprene, latex or others to soften the surface and reduce the risk of trauma to the vascular intima, and the like. Adhesion enhancing surfaces may be provided, such as ePTFE patches or jackets, to promote cellular ingrowth for long term anchoring. In addition, depending upon the deployment system design, the body 66 may be provided with a guidewire lumen extending axially therethrough, to allow the body 66 to be advanced distally over a guidewire during placement at the treatment site.

The device 40 may be implanted within the coronary sinus 22 either through direct surgical (e.g. thoracotomy with or without sternotomy) access, such as in combination with another surgical procedure, via port access, or remotely by way of a percutaneous or surgical cut down access to the venous system. Preferably, the device 40 is implanted in a transluminal procedure, such as by way of a percutaneous access at one of the internal jugular, subdlavian, or femoral veins.

Figure 3:
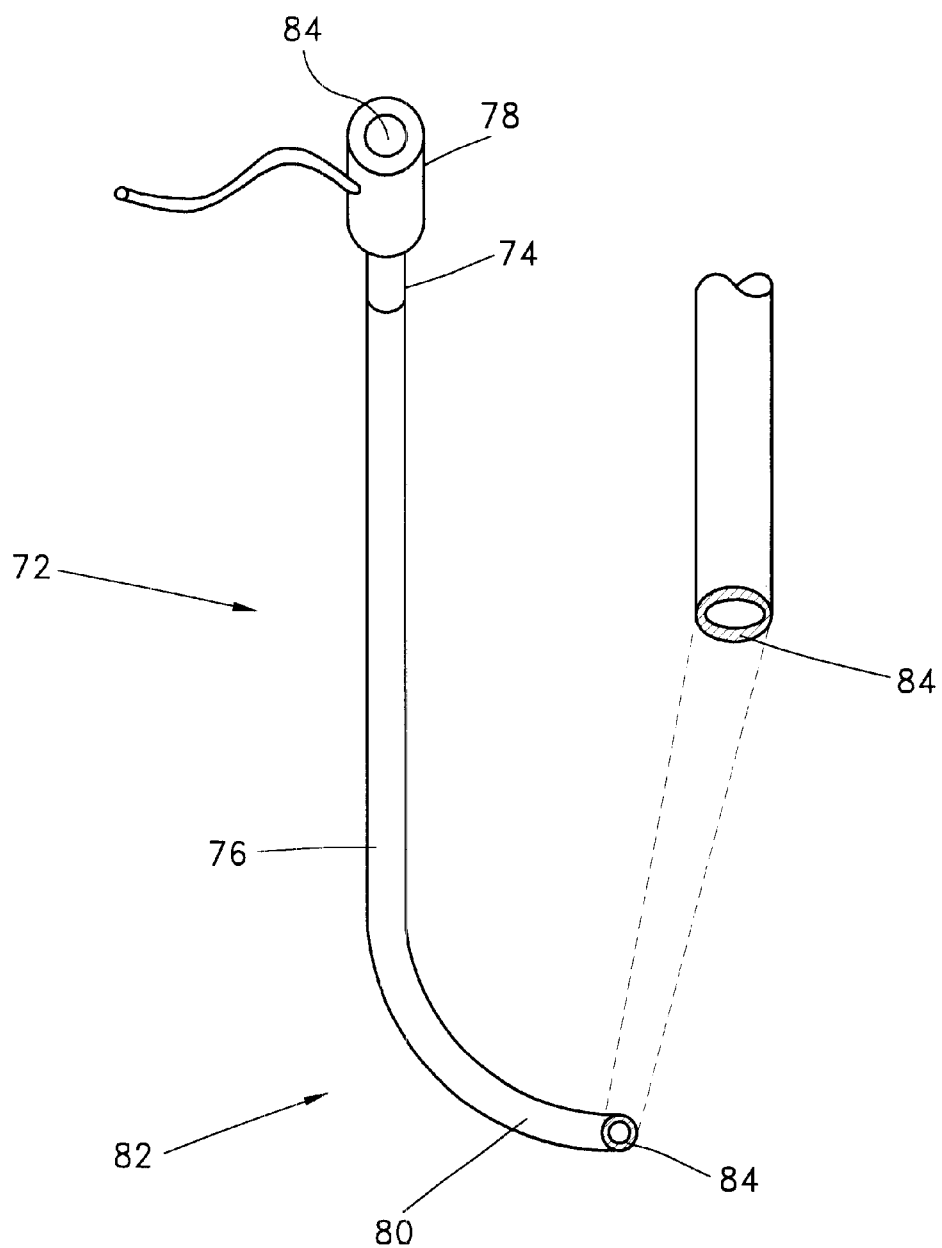
FIG. 3 is an overall view and cross-sectional view through a transvenous delivery sheath.
Figure 4:
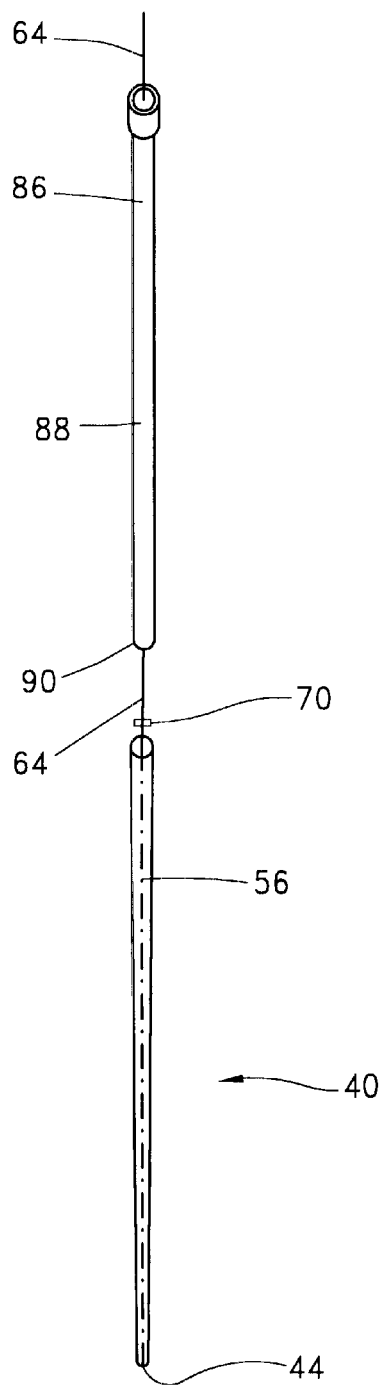
FIG. 4 is a schematic illustration of the delivery sheath and two different embodiments of the implant for extravascular remodeling, one with a forming element and one without.

Referring to FIG. 3, there is disclosed a deployment system 72 for deploying the device 40 of the present invention. The deployment system 72 comprises an introducer sheath or catheter 74, having an elongate flexible tubular body 76 extending from a proximal end 78 to a distal end 80. A preset curve 82 is provided near the distal end 80 of the tubular body 76, as is known in the cardiac access catheter arts. At least one lumen 84 extends through the tubular body 76. In one embodiment, the lumen 84 has a noncircular cross section, such as an ellipse having the major axis perpendicular to the plane of curvature of the introducer sheath 74.

Introducer sheaths are well known in the art, and may be manufactured such as by extrusion, with or without a braided reinforcement structure in the wall. The length and diameter of the introducer sheath 74 may vary considerably, depending upon the dimensions of the device 40 as well as the access point for percutaneous access into the vascular system. For a femoral vein access, for example, the introducer sheath may have a length within the range of from about 80 cm to about 120 cm. Preferably, the outside diameter of the introducer sheath 74 is no more than about 10 French (approximately 3.3 m).

A pusher or dilator 86 has an axial length of from about 10 cm to about 20 cm greater than the axial length of the introducer sheath 74. Dilator 86 has an outside diameter which is less than the inside diameter of the lumen 84, so that the dilator 86 may be freely axially advanced through the lumen 84. The dilator 86 is provided with a central lumen 88, for axially moveably receiving the proximal extension 64 of forming element 56.

When assembled for deployment of a device 40 within the coronary vasculature, a device 40 is positioned within a distal portion of the lumen 84. The dilator 86 is positioned proximal to the device 40 within the lumen 84, and the proximal extension 64 of forming element 56 extends proximally through central lumen 88 of dilator 86. During proximal movement of the introducer sheath 74 with respect to the dilator 86, a distal surface 90 on dilator 86 resists proximal movement of the device 40. Thus, the device 40 may be deployed from the distal end 80 of introducer sheath 74. In addition, proximal retraction of the proximal extension 64 while proximal movement of the device 40 is prevented by surface 90 causes the device 40 to advance from its deployment configuration to its implanted configuration.

Once the coronary sinus 22 has been cannulated by the introducer sheath 74, the dilator that is loaded over the forming element is advanced through the sheath 74. This is used to push the device 40 to the proper location with the distal tip 44 in the distal portion of the great cardiac vein 28. Using counter traction of the forming element and the dilator, the device is curved until the appropriate degree of annular remodeling has been achieved. A locking ring 70 on the forming element that is interposed between the dilator and the device prevents the forming element from slipping distally once the device 40 has been curved. A locking ring 70 that can be released by using a dilator with a different tip geometry may also be employed. After satisfactory deployment and deflection of the device 40, the forming element 56 is cut with a cutting tool (not illustrated) that is placed through the introducer sheath.

A second embodiment of the device is comparable to that described above except that it does not contain an axially moveable forming element. Instead, a core of springy memory material such as nitinol or other NiTi alloy is pre-formed to have the required configuration. When the device is pushed out of the delivery catheter into the coronary venous system, the spring force within the core applies the requisite force to remodel the annulus. This embodiment does not require a tensioning element or a tool to disconnect it from the delivery system. However, the magnitude of force applied to the annulus cannot be adjusted.

A third embodiment is deployed as a loop through the coronary venous system, to form a left ventricular girdle 100. See FIGS. 5–6. The ventricular girdle 100 comprises an elongate flexible body 102 having a proximal end 104 and a distal end 106. A first control line 108 extends proximally from the proximal end 104, and a second control line 110 extends distally from distal end 106. The first and second control lines 108 and 110 may be different portions of the same wire, which extends continuously throughout the length of the body 102. The wire may be a single strand or multi strand component, a length of hypodermic needle tubing, a spring coil, or other structure known in the medical guidewire arts. Preferably, the first and second control lines have a diameter within the range of from about 0.009" to about 0.018", although larger diameters may also be used particularly for the first control line 108.

Figure 5:
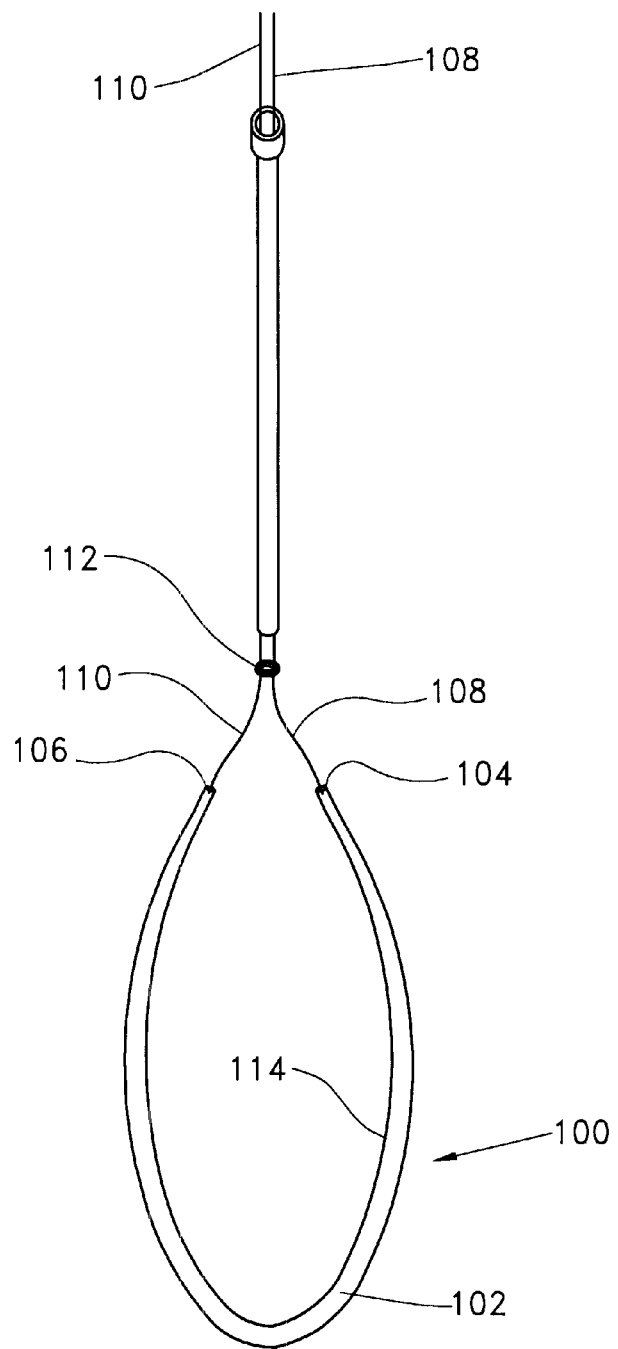
FIG. 5 is a schematic illustration of an alternative embodiment of the present invention positioned in an open-loop configuration through the delivery sheath.

The distal control line 110 is advanced through an introducer sheath into the great cardiac vein 28 and then through anastomotic connections 29 into the middle cardiac vein 30. Continued advancement results in the tip of the distal control line 110 emerging from the ostium 24 of the coronary sinus 22. The control line 110 is then harnessed with a snare and pulled retrogradely through the delivery catheter as illustrated in FIG. 5. The body 102 is then pulled into the coronary venous system. The body is preferably larger in diameter than the first and second control lines 108 and 110, and preferably elliptical or otherwise noncircular in cross section. This shape enlarges the transverse tissue contact surface area and reduces the risk of erosion when tension is applied to the loop. Both the proximal and distal ends of the loop are threaded through a locking clip 112. A dilator is used to push the clip 112 through the delivery catheter to the level of the coronary sinus ostium. Using counter traction on the dilator and the first and second control lines 108 and 110, the clip 112 is cinched on the loop until the requisite degree of tension is produced. Finally, the device is separated from the delivery system using a cutting tool to cut the first and second control lines 108 and 110, and possibly proximal and distal ends 104 and 106 to the extent they extend proximally from clip 112.

Figure 6:
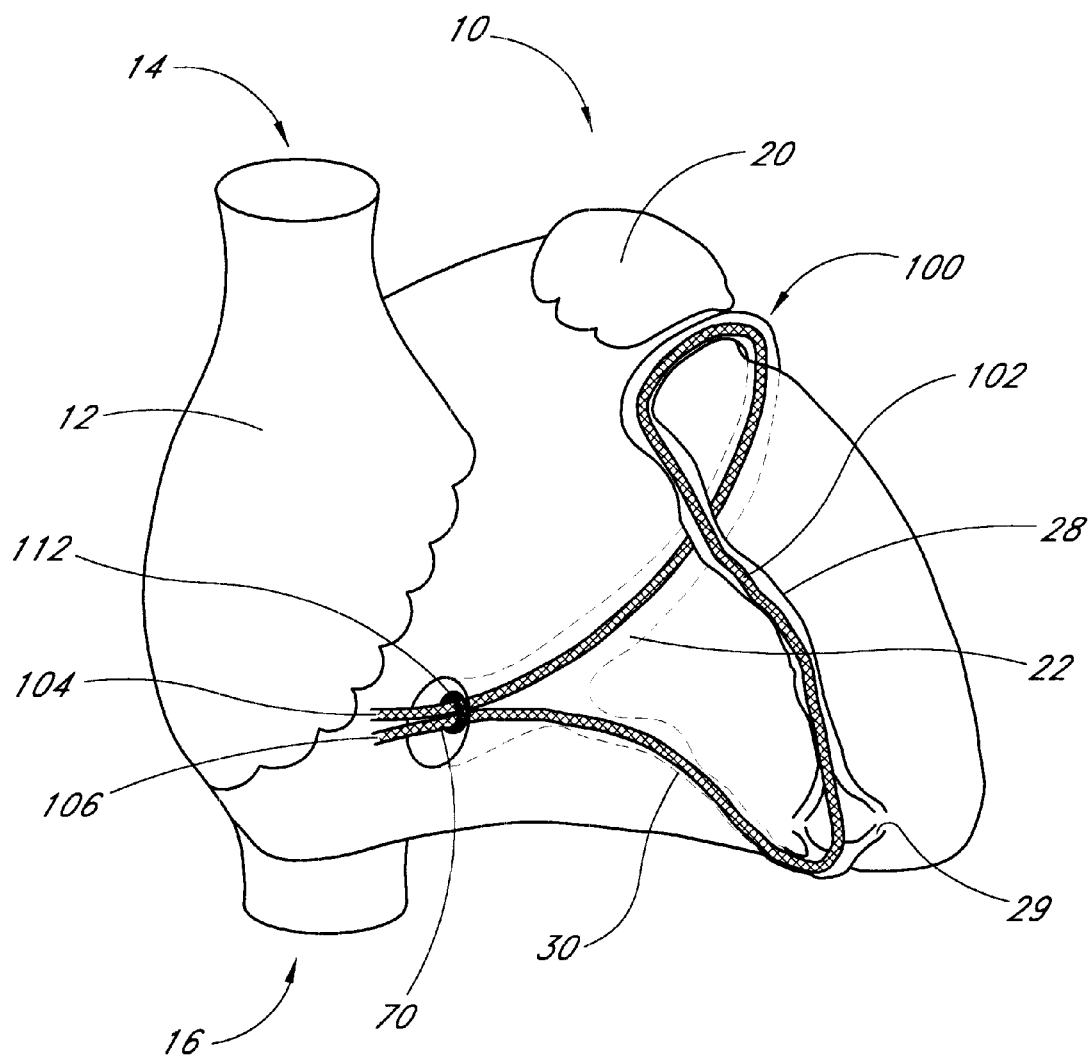
FIG. 6 is a schematic illustration of a heart, having an alternate embodiment of the mitral annuloplasty and cardiac reinforcement device of the present invention positioned within the coronary sinus and contiguous venous system.

The overall length of the embodiment illustrated in FIG. 5 should be sufficient that both of the first control line 108 and second control line 110 can extend outside of the patient, while the body 102 extends throughout the pathway of the ventricular girdle 100 as illustrated in FIG. 6. For a percutaneous femoral vein access, the overall length of the device is therefore preferably at least about 200 cm, and generally within the range of from about 220 cm to about 260 cm. The length of the body 102 from proximal end 104 to distal end 106 is preferably sufficient to form a closed loop as illustrated in FIG. 6. Although both heart size and the shape of the vascular pathway will vary from individual to individual, the length of the body 102 is generally within the range of from about 6 cm to about 12 cm. The body 102 may be injection molded, extruded as a tube, or coextruded over the wire which forms first and second control lines 108 and 110. Preferably, the body 102 either comprises or is coated with a material which is sufficiently compliant to minimize trauma to the vascular intima. Also, the transverse width of a tissue contacting surface 114 on body 102 is preferably sufficient to distribute compressive force to minimize the risks of localized pressure necrosis within the coronary veins.

In each of the foregoing implantation methods, the physician preferably monitors the degree of regurgitation during the step of tightening the implant. Although any reduction in mitral regurgitation may be desirable, regurgitation is preferably reduced to something less than moderate (less than 2+). In any event, at least a one grade reduction is preferably achieved. On the other hand, reconfiguration of the implant should not be accomplished to an extent sufficient to produce mitral stenosis, or any flow limitation of hemodynamic significance.

Thus, the method of implantation preferably further comprises the steps of monitoring the degree of mitral regurgitation during the implantation and/or reconfiguration steps. The degree of mitral regurgitation may be monitored such as by transesophageal echo cardiography, surface echo cardiography, intracardiac echo cardiography, fluoroscopy using radiocontrast in the left ventricle (LV gram), or left atrial or pulmonary capillary wedge pressure tracings, as are understood in the art, during the incremental restriction of the mitral annulus and/or left ventricle step. Once a sufficient reduction in regurgitation has been achieved for a particular patient in the physician's judgement, the device is locked and the proximal extension of the forming element is severed from the device and removed from the patient.

The method may additionally comprise the step of measuring the coronary sinus and/or other coronary vein, and selecting an appropriately sized implant from an array of implants of varying sizes. The appropriately sized implant is thereafter positioned within the target vein. The implant is thus preferably provided in a graduated array of sizes, so that the optimal size can be selected for each patient. The size of the coronary sinus or other vein can be measured using any of a variety of techniques, such as echo cardiogram, MRI, CT scan, or angiography as is understood in the art.

As a further aspect to the present invention, the implant is preferably combined with an appropriate drug therapy for treating congestive heart failure. Residual regurgitation and other hemodynamic functions are preferably measured following implantation of the implant of the present invention. Heart medications are preferably adjusted to take into account the reduction in regurgitation and/or reduction in left ventricle volume in formulating an ongoing drug therapy for the patient.

In accordance with further aspect of the present invention, there is provided a method of constricting the left ventricle. Left ventricular constriction may be desirable in patients without mitral regurgitation. One implementation of this method comprises implanting the ventricular girdle 100 as illustrated, for example, in FIGS. 5 through 6 and previously discussed herein.

Any of the embodiments disclosed herein may additionally be provided with one or more externally facing electrically conductive axially extending strips or annular bands, to enable the device 40 to function additionally as a cardiac pacing or other cardiac electrode. The electrically conductive band or bands are placed in electrical communication with a pacing source or diagnostic instrument by way of one or more electrical conductors extending away from the device 40. The conductors may be electrically connected to any of a wide variety of electronic cardiac rhythm management devices, which are well known in the art.

Although the present invention has been described in terms of certain preferred embodiments, it may be incorporated into other embodiments or performed through other steps by persons of skill in the art in view of the disclosure herein. The scope of the invention is therefore not intended to be limited by the specific embodiments disclosed herein, but is intended to be defined by the full scope of the following claims.

What is claimed is:

1. A medical apparatus for remodeling a mitral valve annulus adjacent to the coronary sinus, comprising:
    an elongate body, having a proximal end region and a distal end region, each of the proximal and distal end regions dimensioned to reside completely within the vascular system, the elongate body being movable from a first configuration for transluminal delivery to at least a portion of the coronary sinus to a second configuration for remodeling the mitral valve annulus proximate the coronary sinus;
    a forming element attached to the elongate body for manipulating the elongate body from the first transluminal configuration to the second remodeling configuration; and
    a lock for retaining the elongate body in the second configuration at least in part within the coronary sinus.

2. The medical apparatus according to claim 1, wherein the forming element is secured to the elongate body at a point of attachment and the forming element is movable relative to the elongate body in order to adjust the elongate body within the coronary sinus between the first and second configurations.

3. The medical apparatus according to claim 2, wherein the forming element is adapted to be severed while the elongate body is positioned at least in part within the coronary sinus in the second configuration.

4. The medical apparatus according to claim 3, further comprising a cutting tool which is adapted to sever the forming element while the elongate body is positioned at least in part within the coronary sinus.

5. A medical apparatus as in claim 1, wherein the elongate body defines an arc when in the remodeling configuration.

6. A medical apparatus as in claim 5, wherein a best fit constant radius curve corresponding to the arc has a radius within the range of from about 10 mm to about 20 mm.

7. A medical apparatus as in claim 1, wherein the lock comprises a locking ring.

8. A medical apparatus as in claim 1, wherein the lock comprises an interference fit.

9. A medical apparatus as in claim 1, wherein the lock comprises an adhesive bond.

10. A medical apparatus as in claim 1, wherein the lock comprises a suture knot.

11. A medical apparatus as in claim 1, wherein the lock comprises a clamp.

12. A medical apparatus as in claim 1, wherein the lock comprises a compression fit.

13. A medical apparatus as in claim 1, wherein the lock comprises a ratchet.

14. A medical apparatus as in claim 1, wherein the lock comprises an engagement surface, which is movable between a first, disengaged configuration and a second, engaged configuration.

15. A medical apparatus as in claim 1, wherein the lock is biased in a locked direction.

16. A medical apparatus as in claim 1, wherein the lock is biased in an unlocked direction.

17. A medical apparatus as in claim 1, further comprising a coating on the body.

18. A medical apparatus as in claim 1, wherein the apparatus is movable from the implantation configuration to the remodeling configuration in response to proximal retraction of the forming element.

19. A medical apparatus as in claim 1, wherein the apparatus is movable from the implantation configuration to the remodeling configuration in response to distal advancement of the forming element.

20. A medical apparatus as in claim 1, further comprising an anchor for retaining the apparatus at a deployment site within a vessel.

21. A medical apparatus as in claim 20, wherein the anchor comprises a distal extension of the apparatus.

22. A medical apparatus as in claim 20, wherein the anchor comprises a friction enhancing surface structure for engaging the wall of the vessel.

23. A medical apparatus as in claim 20, wherein the anchor comprises at least one barb for piercing the wall of the vessel.

24. A medical apparatus as in claim 1, wherein the apparatus has an axial length of no more than about 10 cm.

25. A medical apparatus as in claim 24, wherein the maximum cross sectional dimension through the apparatus is no more than about 10 mm.

26. A medical apparatus as in claim 1, further comprising an axially extending support in the body, attached to the forming element.

27. A medical apparatus as in claim 1, wherein the forming element comprises a polymeric strand.

28. A medical apparatus as in claim 1, wherein the forming element comprises a metal wire.

29. A medical apparatus as in claim 1, wherein the forming element comprises a multifilament structure.

30. A medical apparatus for remodeling a mitral valve annulus adjacent to the coronary sinus, comprising:
   an elongate body, having a proximal end region and a distal end region, each of the proximal and distal end regions dimensioned to reside completely within the vascular system, the elongate body being movable from a first configuration for transluminal delivery to at least a portion of the coronary sinus and a second configuration for remodeling the mitral valve annulus proximate the coronary sinus;
   a forming element attached to the elongate body for manipulating the elongate body from the first transluminal configuration to the second remodeling configuration, the forming element secured to the elongate body at a point of attachment and moveable relative to the elongate body in order to adjust the elongate body within the coronary sinus between the first and second configurations, the forming element adapted to be severed while the elongate body is positioned at least in part within the coronary sinus in the second configuration; and
   a cutting tool which is adapted to sever the forming element while the elongate body is positioned at least in part within the coronary sinus;
   wherein the elongate body maintains a substantially constant length when manipulated by the forming element between the first and second configurations.

31. A medical apparatus for remodeling a mitral valve annulus adacent to the coronary sinus, comprising:
   an elongate body, having a proximal end region and a distal end region, each of the proximal and distal end regions dimensioned to reside completely within the vascular system, the elongate body being movable from a first configuration for transluminal delivery to at least a portion of the coronary sinus and a second configuration for remodeling the mitral valve annulus proximate the coronary sinus;
   a forming element attached to the elongate body for manipulating the elongate body from the first transluminal configuration to the second remodeling configuration, the forming element secured to the elongate body at a point of attachment and movable relative to the elongate body in order to adjust the elongate body within the coronary sinus between the first and second configurations, the forming element adapted to be severed while the elongate body is positioned at least in part within the coronary sinus in the second configuration; and
   a cutting tool adapted to sever the forming element while the elongate body is positioned at least in part within the coronary sinus;
   wherein the elongate body is relatively non-compressible while the elongate body is adjusted between the first and second configurations.

32. A medical apparatus for remodeling a mitral valve annulus adjacent to the coronary sinus, comprising:
   an elongate body, having a proximal end region and a distal end region, each of the proximal and distal end regions dimensioned to reside completely within the vascular system, the elongate body being movable from a first configuration for transluminal delivery to at least a portion of the coronary sinus and a second configuration for remodeling the mitral valve annulus proximate the coronary sinus;
   a forming element attached to the elongate body for manipulating the elongate body from the first transluminal configuration to the second remodeling configuration, the forming element secured to the elongate body at a point of attachment and movable relative to the elongate body in order to adjust the elongate body within the coronary sinus between the first and second configurations, the forming element adapted to be severed while the elongate body is positioned at least in part within the coronary sinus in the second configuration; and
   a cutting tool adapted to sever the forming element while the elongate body is positioned at least in part within the coronary sinus;
   wherein the elongate body is interchangeably adjustable between the first and second configurations within the coronary sinus.

33. A method of performing transluminal mitral annuloplasty, comprising the steps of:
   selecting a prosthesis having a proximal end and a distal end;
   providing a deployment system cooperating with the prosthesis and which is adapted to at least in part deliver the prosthesis into the coronary sinus;
   inserting the deployment system and prosthesis into the venous system;
   transluminally advancing the prosthesis into at least a portion of the coronary sinus;
   tightening the prosthesis to generate a compressive force on the adjacent cardiac musculature and influence the size of the mitral valve annulus, the tightening step achieved by proximally retracting a forming element while resisting proximal movement of the prosthesis; and
   locking the prosthesis after the step of tightening;
   wherein the prosthesis is interchangeably adjustable between tightening to generate the compressive force, and untightening to relieve the compressive force while the prosthesis is positioned within the coronary sinus.

34. A method as in claim 33, further comprising the step of percutaneously accessing the venous system prior to the transluminally advancing step.

35. A method as in claim 33, wherein the accessing step is accomplished by accessing one of the internal jugular, subclavian and femoral veins.

36. A method as in claim 33, further comprising the step of limiting diastolic expansion of the left ventricle.

37. A method as in claim 33, wherein the transluminally advancing step is accomplished using a catheter.

38. A method as in claim 33, wherein the locking step comprises moving an engagement surface from a disengaged configuration to an engaged configuration.

39. A method as in claim 33, wherein the locking step comprises providing an interference fit.

40. A method as in claim 33, wherein the locking step comprises providing an adhesive bond.

41. A method as in claim 33, wherein the locking step comprises providing a knot.

42. A method as in claim 33, wherein the locking step comprises providing a compression fit.

43. A method as in claim 33, further comprising the steps of first measuring the coronary sinus and then selecting an appropriately sized prosthesis prior to the inserting step.

44. A method as in claim 33, further comprising the step of measuring hemodynamic function following the locking step.

45. A method as in claim 44, further comprising the step of determining an ongoing drug therapy taking into account the post implantation hemodynamic function.

46. A method of performing trasluminal mitral annuloplasty, comprising the step of:

selecting a prosthesis having a proximal end and a distal end;

providing a deployment system cooperating with the prosthesis and which is adapted to at least in part deliver the prosthesis into the coronary sinus;

inserting the deployment system and prosthesis into the venous system;

transluminally advancing the prosthesis into at least a portion of the coronary sinus;

tightening the prosthesis to generate a compressive force on the adjacent cardiac musculature and influence the size of the mitral valve annulus, the tightening step achieved by proximally retracting a forming element while resisting proximal movement of the prosthesis; and locking the prosthesis after the step of tightening;

wherein the prosthesis maintains a substantially constant length when tightened to generate the compressive force.

* * * * *